United States Patent
Coburn et al.

(10) Patent No.: US 9,550,740 B2
(45) Date of Patent: Jan. 24, 2017

(54) ANTIMICROBIAL COMPOUNDS

(71) Applicants: Dow Global Technologies LLC, Midland, MI (US); Rohm and Haas Company, Philadelphia, PA (US)

(72) Inventors: Charles E. Coburn, Vernon Hills, IL (US); Thomas Koehler, Kreuzlingen (CH); Heather R. Mcginley, Highland Park, IL (US); Asghar A. Peera, Cary, IL (US)

(73) Assignees: ROHM AND HAAS COMPANY, Philadelphia, PA (US); DOW GLOBAL TECHNOLOGIES LLC, Midland, MI (US)

( * ) Notice: Subject to any disclaimer, the term of this patent is extended or adjusted under 35 U.S.C. 154(b) by 206 days.

(21) Appl. No.: 14/565,890

(22) PCT Filed: Jun. 12, 2013

(86) PCT No.: PCT/US2013/045408
§ 371 (c)(1),
(2) Date: Dec. 10, 2014

(87) PCT Pub. No.: WO2013/191986
PCT Pub. Date: Dec. 27, 2013

(65) Prior Publication Data
US 2016/0176828 A1    Jun. 23, 2016

Related U.S. Application Data

(60) Provisional application No. 61/661,515, filed on Jun. 19, 2012.

(51) Int. Cl.
C07D 265/06 (2006.01)
C07D 263/06 (2006.01)
A01N 43/86 (2006.01)
A01N 43/76 (2006.01)

(52) U.S. Cl.
CPC .............. C07D 265/06 (2013.01); A01N 43/76 (2013.01); A01N 43/86 (2013.01); C07D 263/06 (2013.01)

(58) Field of Classification Search
CPC ..... C07D 265/06; C07D 263/06; A01N 43/86; A01N 43/76

USPC ........................... 544/72, 96; 514/228.8, 374
See application file for complete search history.

(56) References Cited

U.S. PATENT DOCUMENTS

| | | |
|---|---|---|
| 5,108,740 A | 4/1992 | Greenwald et al. |
| 5,480,643 A | 1/1996 | Donovan et al. |
| 6,034,138 A | 3/2000 | Synodis et al. |
| 7,319,131 B2 | 1/2008 | Swedo et al. |
| 8,741,928 B2 | 6/2014 | Coburn et al. |
| 2009/0131294 A1 | 5/2009 | Bettiol et al. |
| 2013/0267604 A1 | 10/2013 | Coburn et al. |

FOREIGN PATENT DOCUMENTS

WO    0063329 A1    10/2000

OTHER PUBLICATIONS

Ebara et al. Journal of Organic Chemistry (2011), 76(15), 6464 (Abstract).*
Power, "aldehydes as biocides", Progress in Medicinal Chemistry, vol. 34, pp. 149-210 (1997).
Min, et al., "Synthesis of an oxazolidine series and its tanning properties", J. Northwest University, No. 1, pp. 11-30 (1988).

* cited by examiner

*Primary Examiner* — Kahsay Habte
(74) *Attorney, Agent, or Firm* — Tifani M. Edwards

(57) ABSTRACT

Provided are compounds which are useful for controlling microorganisms in aqueous or water-containing systems or in systems which are exposed to moisture, including at elevated temperature. The antimicrobial compounds are of the formula I:

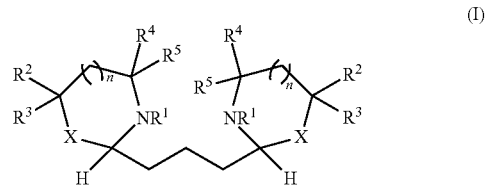

wherein n, $R^1$, $R^2$, $R^3$, $R^4$, $R^5$, and X are as defined herein.

9 Claims, No Drawings

ANTIMICROBIAL COMPOUNDS

FIELD

The invention relates generally to antimicrobial compounds and methods of their use for the control of microorganisms in aqueous or water-containing systems or in systems which are exposed to moisture.

BACKGROUND

Protecting aqueous systems from microbial contamination is critical to the success of many industrial processes, including oil or natural gas production operations. In oil and gas operations, microorganism contamination from both aerobic and anaerobic bacteria can cause serious problems such as reservoir souring (mainly caused by anaerobic sulfate-reducing bacteria (SRB)), microbiologically influenced corrosion (MIC) on metal surfaces of equipment and pipelines, and degradation of polymer additives.

Glutaraldehyde is a known antimicrobial compound that is used to control the growth of microorganisms in aqueous systems and fluids, including those found in oil and gas operations. Glutaraldehyde, however, is susceptible to a number of drawbacks. For instance, it can degrade over time at the elevated temperatures often encountered in the oil and gas production environment. The material can also be inactivated by other common oilfield chemicals such as bisulfate salts and amines. These conditions can leave oilfield infrastructure (wells, pipelines, etc.) and formations susceptible to microbial fouling.

The problem addressed by this invention is the provision of antimicrobial systems with improved thermal and chemical stability.

STATEMENT OF INVENTION

We have now found that compounds of formula I as described herein are capable of controlling microorganisms in aqueous or water-containing systems or in systems which are exposed to moisture, including those found in oil and gas operations. Advantageously, unlike the free aldehyde, the compounds of formula I are more stable at elevated temperatures, thus permitting extended control of microbial fouling. In addition, the compounds may exhibit improved stability in the presence of other chemical species that would otherwise degrade the free glutaraldehyde, such as reducing or oxidizing agents including bisulfites, and amines.

In one aspect, therefore, the invention provides compounds of formula I:

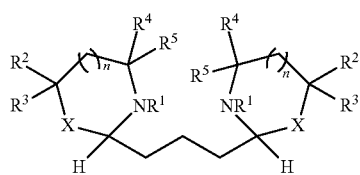

(I)

wherein n is 0 or 1;
$R^1$ is linear or branched $C_1$-$C_{10}$ alkyl;
$R^2$ is H, linear or branched $C_1$-$C_{10}$ alkyl, $C_3$-$C_8$ cycloalkyl, or aryl;
$R^3$, $R^4$, and $R^5$ at each occurrence are independently H, linear or branched $C_1$-$C_{10}$ alkyl, or $C_3$-$C_8$ cycloalkyl;
or $R^2$ and $R^3$ together with the carbon to which they are attached form $C_3$-$C_8$ cycloalkyl;
or $R^4$ and $R^5$ together with the carbon to which they are attached form $C_3$-$C_8$ cycloalkyl; and
X is O or $NR^6$, wherein $R^6$ is linear or branched $C_1$-$C_6$ alkyl.

In another aspect, the invention provides methods for controlling microorganisms in aqueous or water-containing systems, or in systems which are exposed to moisture. In some embodiments, the aqueous or water-containing system has a temperature of at least 40° C. The method comprises contacting the aqueous or water-containing system with a compound of formula I as described herein.

DETAILED DESCRIPTION

"Alkyl," as used in this specification encompasses straight and branched chain aliphatic groups having the indicated number of carbon atoms. Exemplary alkyl groups include, without limitation, methyl, ethyl, propyl, isopropyl, butyl, isobutyl, sec-butyl, tert-butyl, pentyl, hexyl, heptyl, and octyl.

The term "cycloalkyl" refers to saturated and partially unsaturated cyclic hydrocarbon groups having the indicated number of ring carbon atoms. Preferred cycloalkyl groups include, without limitation, cyclopentyl, cyclohexyl, cycloheptyl, and cyclooctyl. The cycloalkyl is optionally substituted with linear or branched $C_1$-$C_6$ alkyl.

An "aryl" group is a C6-C12 aromatic moiety comprising one to three aromatic rings. Preferably, the aryl group is a C6-C10 aryl group. Preferred aryl include, without limitation, phenyl, naphthyl, anthracenyl, and fluorenyl. More preferred is phenyl.

For the purposes of this specification, the meaning of "microorganism" includes, but is not limited to, bacteria, fungi, algae, archaea, and viruses. The words "control" and "controlling" should be broadly construed to include within their meaning, and without being limited thereto, inhibiting the growth or propagation of microorganisms, killing microorganisms, disinfection, and/or preservation against microorganism re-growth. In some embodiments, the microorganisms are bacteria. In some embodiments, the microorganisms are aerobic bacteria. In some embodiments, the microorganisms are anaerobic bacteria. In some embodiments, the microorganisms are sulfate reducing bacteria (SRB). In some embodiments, the microorganisms are acid producing bacteria (APB). In some embodiments, the microorganisms are archaea.

Unless otherwise indicated, numeric ranges, for instance as in "from 2 to 10," are inclusive of the numbers defining the range (e.g., 2 and 10).

Unless otherwise indicated, ratios, percentages, parts, and the like are by weight.

As noted above, the invention provides compounds and methods of using them for the control of microorganisms in aqueous or water-containing systems or in systems which are exposed to moisture, including those found in oil and gas operations.

Compounds of the invention may be represented by the formula I:

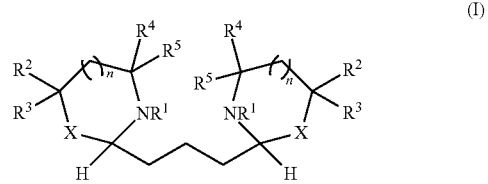

(I)

wherein n is 0 or 1;

$R^1$ is linear or branched $C_1$-$C_{10}$ alkyl;

$R^2$ is H, linear or branched $C_1$-$C_{10}$ alkyl, $C_3$-$C_8$ cycloalkyl, or aryl;

$R^3$, $R^4$, and $R^5$ at each occurrence are independently H, linear or branched $C_1$-$C_{10}$ alkyl, or $C_3$-$C_8$ cycloalkyl;

or $R^2$ and $R^3$ together with the carbon to which they are attached form $C_3$-$C_8$ cycloalkyl;

or $R^4$ and $R^5$ together with the carbon to which they are attached form $C_3$-$C_8$ cycloalkyl; and X is O or $NR^6$, wherein $R^6$ is linear or branched $C_1$-$C_6$ alkyl.

In some embodiments, X in the compounds of formula I is O.

In some embodiments, X is $NR^6$, wherein $R^6$ is linear or branched $C_1$-$C_4$ alkyl.

In some embodiments, n is 0.

In some embodiments, n is 1.

In some embodiments, $R^1$ is linear or branched $C_1$-$C_8$ alkyl.

In some embodiments, $R^2$ is aryl, preferably phenyl.

In some embodiments, $R^2$ is H.

In some embodiments, $R^2$, $R^3$, $R^4$, and $R^5$ are each H.

In some embodiments, n is 1, $R^2$ is aryl (preferably phenyl), $R^3$, $R^4$, and $R^5$ are each H, and X is O.

In some embodiments, n is 0, $R^2$, $R^3$, $R^4$, and $R^5$ are each H, and X is O.

Exemplary compounds of formula I include the following:

In some embodiments, 1,3-bis(3-methyloxazolidin-2-yl)propane is excluded as a compound of the invention.

Compounds of formula I may be prepared, for example, as depicted in Scheme I. Typically, the glutaraldehyde is mixed with two or more equivalents of amine compound A in a suitable solvent, such as water or ethylacetate. The mixture may be stirred for sufficient time to allow the reaction to occur and the desired compound of formula I to form. The product may be used as is, or optionally further purified using techniques well known to those skilled in the art, such as crystallization, chromatography, distillation, extraction, etc.

SCHEME I

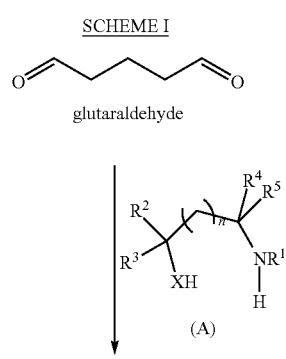

| Name | Structure |
|------|-----------|
| 1,3-bis(3-methyloxazolidin-2-yl)propane | 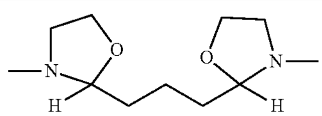 |
| 1,3-bis(3-butyloxazolidin-2-yl)propane | 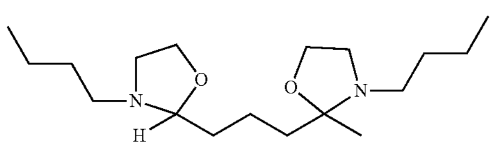 [SMILES: CCCCN1CCOC1CCCC1(C)OCCN1CCCC] |
| 1,3-bis(3-octyloxazolidin-2-yl)propane | 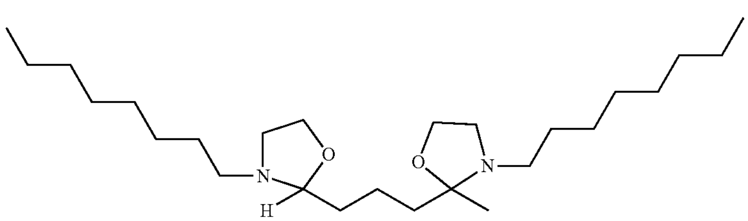 [SMILES: CCCCCCCCN1CCOC1CCCC1(C)OCCN1CCCCCCCC] |
| 1,3-bis(3-methyl-6-phenyl-1,3-oxazinan-2-yl)propane | 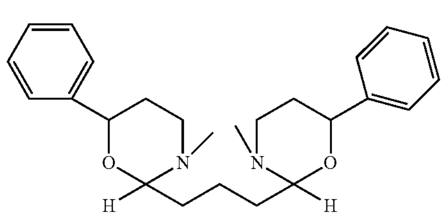 [SMILES: CN1CCC(c2ccccc2)OC1CCCC1OC(c2ccccc2)CCN1C] |

-continued

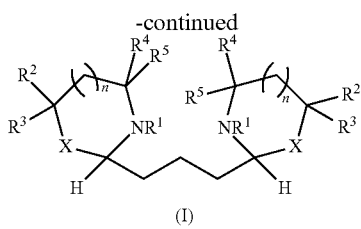

(I)

The compound A used in the synthesis described above is generally a secondary amine compound that contains an additional secondary amine or hydroxyl group. Examples include: 3-(methylamino)-1-phenylpropan-1-ol, 2-(octylamino)ethanol, 2-(methylamino)ethanol, or 2-(butylamino) ethanol. Such compounds may be commercially available and/or may be readily prepared by those skilled in the art.

As noted above, it is not necessary in the invention that the compounds of formula I be isolated or purified from the reaction mixture in which they were synthesized, and in some embodiments it may be preferred that the reaction mixture be used without purification for the control of microorganisms. Such mixture may contain isomers of the compound, or polymeric species or other byproducts that are inert or that may also provide microbial control.

The compounds of formula I may release glutaraldehyde when heat-activated. Unlike the free aldehyde, however, the compounds are more stable at elevated temperatures thus permitting extended control of microbial fouling. In addition, the compounds may exhibit improved stability in the presence of other chemical species that would otherwise degrade the free aldehydes, such as bisulfites, and amines.

Because of their stability and heat activation characteristics, the compounds of the invention are useful for controlling microorganisms for extended periods of time in aqueous or water-containing systems or in systems which are exposed to moisture, including those that are at elevated temperatures. The compounds of the invention are also useful for incorporation into products which are manufactured or stored at elevated temperatures. The compounds are also useful for controlling microorganisms aqueous or water-containing systems that may be present or used in oil or natural gas applications, paper machine white water, industrial recirculating water, starch solutions, latex or polymer emulsions, coatings or building products or household products or personal care products which are manufactured at elevated temperatures, plastics, hot rolling machining fluids, or industrial dishwashing or laundry fluids, animal biosecurity fluids, or high level disinfection fluids. In some embodiments, the aqueous or water-containing system may be present or used in oil or natural gas applications. Examples of such systems include, but are not limited to, fracturing fluids, drilling fluids, water flood systems, oil field water, and produced fluids.

In some embodiments, the system may be at a temperature of 40° C. or greater, alternatively 55° C. or greater, alternatively 60° C. or greater, alternatively 70° C. or greater, or alternatively 80° C. or greater.

In addition to their heat stability, the compounds may further be effective when a deactivating agent, such as a source of bisulfite ion or amines is present in the system.

A person of ordinary skill in the art can readily determine, without undue experimentation, the effective amount of the compound that should be used in any particular application to provide microbial control. By way of illustration, a suitable concentration, based on the equivalent of glutaraldehyde that is potentially released (assuming 100% release) by the formula I compound is typically at least about 1 ppm, alternatively at least about 5 ppm, alternatively at least about 50 ppm, or alternatively at least about 100 ppm by weight. In some embodiments, the concentration is 2500 ppm or less, alternatively 1500 ppm or less, or alternatively 1000 ppm or less. In some embodiments, the aldehyde equivalent concentration is about 100 ppm.

The compounds of formula I may be used in the system with other additives such as, but not limited to, surfactants, ionic/nonionic polymers and scale and corrosion inhibitors, oxygen scavengers, nitrate or nitrite salts, and/or additional antimicrobial compounds.

Some embodiments of the invention will now be described in detail in the following Examples.

EXAMPLES

Example 1

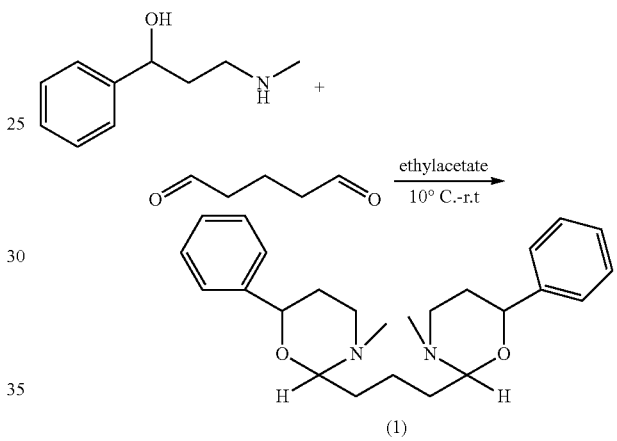

A three neck 50 mL round bottom flask equipped with a stir bar, thermocouple, addition funnel capped with nitrogen inlet and condenser is charged with 3-(methylamino)-1-phenylpropan-1-ol (100%, 8.26 g, 0.05 mols, 2.0 equivalents) and dissolved in 15 mL of ethylacetate. The flask is cooled to approximately 10° C. under ice/water bath. Once the temperature is reached, glutaraldehyde (50%, 5.0 g, 0.025 mols, 1.0 equivalents) is added drop wise over a period of 5-10 minutes. The reaction temperature is maintained by cooling the bath and by controlled addition of glutaraldehyde. After complete addition of glutaraldehyde, the reaction can still be stirred. However, as the reaction mixture warms to room temperature the reaction mixture becomes opaque and solids start forming. The reaction is stopped and the solid filtered through a Buchner funnel and washed thoroughly with pentane. The white powder is dried under vacuum for 1 h. This process results in 1.5 g of white solid (8% yield). The material does not elute in the GC and therefore is characterized by LC-MS. The LC-MS analysis confirms the presence of (1) 1,3-bis(3-methyl-6-phenyl-1,3-oxazinan-2-yl)propane and CI-LC/MS shows [M+H]=395.

Example 2

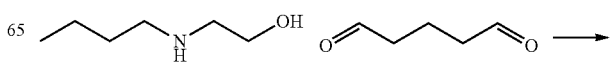

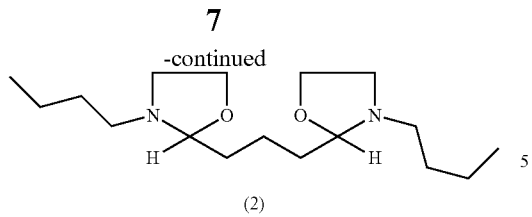

(2)

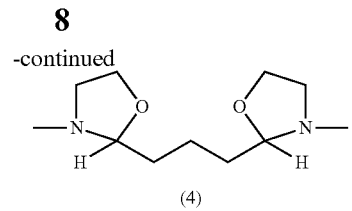

(4)

A three neck 50 mL round bottom flask equipped with a stir bar, thermocouple, addition funnel capped with nitrogen inlet and condenser is charged with 2-(butylamino)ethanol (98%, 5.1 g, 0.042 mols, 2.0 equivalents) and the flask is cooled to approximately 10° C. under ice/water bath. Once the temperature is reached, glutaraldehyde (50%, 4.27 g, 0.021 mols, 1.0 equivalents) is added drop wise over a period of 5-10 minutes. The reaction temperature is maintained by cooling the bath and by controlled addition of glutaraldehyde. After complete addition of glutaraldehyde, the reaction can still be stirred but becomes opaque. GC of the reaction mixture shows the presence of the unreacted amine, the mono oxazolidine adduct (4-(3-butyloxazolidin-2-yl)butanal) and the desired compound (2) peaks. The reaction is stopped and the content of the flask dissolved in 25 mL ethyl acetate and washed thrice with 25 mL water. The resulting organic layer is kept under the rotovap to strip off all the solvent. The GC of the stripped off material, still shows the presence of starting amine and the mono oxazolidine adduct (4-(3-butyloxazolidin-2-yl)butanal). At this time, the content is heated to 40° C. to drive the mono adduct to the desired bis oxazolidine. This process results in 4.60 g of crude yellow liquid (73% yield). The GC-MS analysis confirms the presence of (2) 1,3-bis(3-butyloxazolidin-2-yl) propane and CI-GC/MS shows [M+H]=299.

Example 3

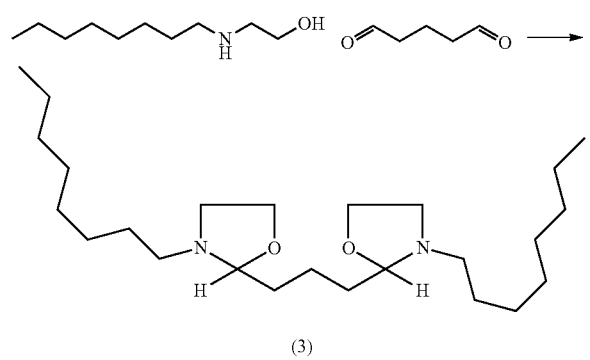

(3)

Compound 3 may be prepared through substantially the same procedure as described in Example 2, using 2-(octylamino)ethanol as the starting amine Example 4

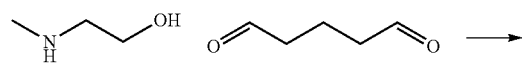

Compound 4 may be prepared through substantially the same procedure as described in Example 2, using 2-(methylamino)ethanol as the starting amine Example 5

Assay for Biocidal Efficacy

Assay for Biocidal Efficacy at Room Temperature: Glutaraldehyde and Compounds 1 and 4 are tested for biocidal activity against a pool of aerobic organisms at room temperature and against sulfate reducing bacteria (SRB) at room temperature. Tests are performed as follows:
a. Stock preparation. Glutaraldehyde (50% in water) and Compounds 1 and 4 are each dissolved in DMSO to a concentration of 200 mM, which is equivalent to 20,000 ppm of free glutaraldehyde.
b. Aerobic Bacteria—a mixed pool of 6 bacterial species at approximately $5 \times 10^6$ CFU/mL in phosphate buffered saline is distributed into a 96-well plate. Each well receives an independent chemical treatment of the tested compounds at concentrations ranging from 200 ppm to 12 ppm glutaraldehyde. A control treatment of DMSO alone is also included. Each condition is tested in triplicate. After set periods of incubation (1, 4, and 24 h), the number of surviving cells in each well are enumerated by dilution to extinction in a medium containing resazurin dye as an indicator.
c. Sulfate Reducing Bacteria (SRB)—SRB testing is performed as for the aerobic bacteria with the following modifications: the species Desulfovibrio longus is tested in anaerobic PBS and the enumeration of surviving cells is performed in a medium containing soluble iron as an indicator.
d. Results: Values indicate minimum the dose needed (in ppm) to achieve 3-log reduction in bacteria levels. "n/a" indicates the threshold is not met at any of the tested doses. "N.D." indicates no data available.

| bacteria type | 1 hour | | | 4 hours | | | 24 hours | | |
|---|---|---|---|---|---|---|---|---|---|
| | glut | 1 | 4 | glut | 1 | 4 | glut | 1 | 4 |
| aerobic | 26 | 59 | n/a | 26 | 26 | 200 | 26 | 40 | 200 |
| SRB | 89 | 133 | 200 | 18 | 133 | 133 | <12 | N.D | N.D. |

Compound 1 shows significant biocidal activity against aerobic bacteria at room temperature. Compound 4 has limited activity under these conditions. Both show some activity against SRB, but are not as effective as glutaraldehyde.

Assay for Biocidal Efficacy at Elevated Temperature

Compound 1 is dissolved in DMSO to yield a 200 mM solution such that the glutaraldehyde-equivalent concentration of the stock solution is 20,000 ppm. The bacterial strain Thermus thermophilus (ATCC 27634) is maintained at 70° C. After 24-48 hours of growth, 10 mL of bacterial culture is harvested by spinning in a Beckman-Coulter benchtop centrifuge at 3000 rpm for 15 min. The cell pellet is resuspended in 100 mL of phosphate-buffered saline (PBS) to give approximately $5 \times 10^5$ CFU/mL and aliquoted into 10 mL portions in glass test tubes fitted with screw caps. Samples are equilibrated to 37, 55, or 70° C. for 30 min and then treated with glutaraldehyde or Compound 1 at 50 ppm glutaraldehyde equivalent. The treated samples are returned to their respective equilibration temperatures for 4 h and then enumerated for surviving bacteria. After 24 h, the process is repeated by adding fresh grown bacteria to the samples to re-challenge the biocide. The samples are again enumerated after 4 h.

Results are reported in terms of log kill of treated bacterial populations relative to an untreated control at each temperature. For values listed as ">x," actual kill may have been higher but could not be detected by this assay. Compound 1 shows equivalent activity to glutaraldehyde at each temperature tested.

| temperature | 4 hr | | 24 hr | |
| --- | --- | --- | --- | --- |
| | glut | 1 | glut | 1 |
| 37 C. | >3 | >3 | >4 | >4 |
| 55 C. | >3 | >3 | >3 | >3 |
| 70 C. | >4 | >4 | >4 | >4 |

We claim:
1. A compound of formula I:

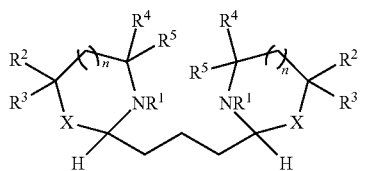

(I)

wherein n is 0 or 1;
$R^1$ is linear or branched $C_1$-$C_{10}$ alkyl;
$R^2$ is H, linear or branched $C_1$-$C_{10}$ alkyl, $C_3$-$C_8$ cycloalkyl, or aryl;
$R^3$, $R^4$, and $R^5$ at each occurrence are independently H, linear or branched $C_1$-$C_{10}$ alkyl, or $C_3$-$C_8$ cycloalkyl;
or $R^2$ and $R^3$ together with the carbon to which they are attached form $C_3$-$C_3$ cycloalkyl;
or $R^4$ and $R^5$ together with the carbon to which they are attached form $C_3$-$C_3$ cycloalkyl; and
X is O or $NR^6$, wherein $R^6$ is linear or branched $C_1$-$C_6$ alkyl.

2. The compound of claim 1 n is 1, $R^2$ is aryl and $R^3$, $R^4$, and $R^5$ are each H.

3. The compound of claim 1 wherein n is 0, and $R^2$, $R^3$, $R^4$, and $R^5$ are each H.

4. The compound of claim 1 wherein X is O.

5. The compound of claim 1 that is: 1,3-bis(3-methyloxazolidin-2-yl)propane; 1,3-bis (3-butyloxazolidin-2-yl)propane; 1,3-bis(3-octyloxazolidin-2-yl)propane; or 1,3-bis(3-methyl-6-phenyl-1,3-oxazinan-2-yl)propane.

6. A method for controlling microorganisms in an aqueous or water-containing system or in a system which is exposed to moisture, the method comprising contacting the system with the compound of claim 1.

7. The method of claim 6 wherein the system is at a temperature of at least 40° C.

8. The method of claim 6 wherein the system is an oil or gas field fluid, paper machine white water, industrial recirculating water, a starch solution, a latex or polymer emulsion, a coating or building product or household product or personal care product which is manufactured at elevated temperature, a plastic, a hot rolling machining fluid, an industrial dishwashing or laundry fluid, an animal biosecurity fluid, or a high level disinfection fluid.

9. The method of claim 6 wherein the system is a fracturing fluid, a drilling fluid, a water flood system, an oil field water, or a produced fluid.

* * * * *